United States Patent [19]

Baum et al.

[11] 4,139,403
[45] Feb. 13, 1979

[54] DINITROALKYL AND FLUORODINITROALKYL SILICON COMPOUNDS

[75] Inventors: Kurt Baum, Pasadena; Duane A. Lerdal, Sierra Madre; Jerald S. Horn, Granada Hills, all of Calif.

[73] Assignee: The United States of America as represented by the Secretary of the Navy, Washington, D.C.

[21] Appl. No.: 826,212

[22] Filed: Aug. 19, 1977

[51] Int. Cl.² .............................................. C07F 7/10
[52] U.S. Cl. .............................. 149/88; 260/448.2 N; 260/448.2 E; 149/23
[58] Field of Search .................. 260/448.2 N, 448.2 E; 149/88, 23

[56] References Cited

U.S. PATENT DOCUMENTS

| | | | |
|---|---|---|---|
| 2,756,246 | 7/1956 | Burkhard | 260/448.2 N |
| 2,985,680 | 5/1961 | Pepe | 260/448.8 R |
| 3,007,957 | 11/1961 | Bailey et al. | 260/448.2 N X |
| 3,020,302 | 2/1962 | Bailey et al. | 260/448.2 N |
| 3,375,218 | 3/1968 | Bailey et al. | 260/448.2 N X |
| 3,655,555 | 4/1972 | Rossmy et al. | 260/448.2 N X |
| 3,898,255 | 8/1975 | Meiller | 260/448.2 N |

OTHER PUBLICATIONS

"Chem. Abstracts", 49, p. 1541, 1955.
"J.A.C.S.", 78, pp. 1501–1504, 1956.
"J.A.C.S.", 83, p. 3535, 1961.
"J.A.C.", 73, pp. 4770–4773, 1951.
"J. Org. Chem.", 33, pp. 3073–3080, 1968.

Primary Examiner—Paul F. Shaver
Attorney, Agent, or Firm—R. S. Sciascia; W. Thom Skeer; L. E. K. Pohl

[57] ABSTRACT

Energetic silicon compounds of the general formulae

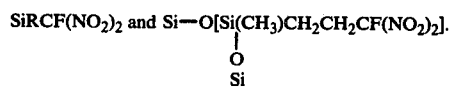

The gem dinitro compounds are prepared from alkyl bromide silanes by sodium nitrite displacement and oxidative nitration. The compounds are then fluorinated. To prepare the polysiloxanes, phenyl blocking groups are used during synthesis of the fluoro dinitro moiety and are then replaced with bromine and the monomer is hydrolyzed.

17 Claims, No Drawings

DINITROALKYL AND FLUORODINITROALKYL SILICON COMPOUNDS

BACKGROUND OF THE INVENTION

The present invention relates to dinitro and fluorodinitroalkyl silicon compounds and more particularly to gem dinitrosubstituted silanes and polysiloxanes useful as energetic components of rocket propellants and explosives.

Nitro compounds were contained in the first recorded experiments with explosives as potassium nitrate in gunpowder. The important explosives TNT and nitrocellulose are, of course, also nitro compounds. Nitroglycerin is an aliphatic di-or tri-nitro compound. Gem, meaning twin, dinitro compounds have two nitro groups on the same carbon atom. They first became of interest after work on tetranitromethane was declassified after World War II. Tetranitromethane is sometimes considered an oxidizing agent rather than an explosive, although gem dinitro compounds are generally recognized as useful in the explosive arts.

Although not previously embodied in explosive compounds, the silicon-carbon bond is generally recognized as imparting favorable high temperature stability as well as low temperature fluid properties to organic compounds. Silicones are thermally and oxidatively stable and can retain flexibility or fluidity at very low temperatures. Silicones are characterized by their silicon-oxygen backbones. They commonly range from 24 monomer units in fluids up to 10,000 units in elastomers. Their properties are varied by varying the organic side chains on the silicon atom. For instance, methyl groups add thermal stability, phenyl groups impart oxidative stability, and vinyl groups are used for crosslinking. Although the chemistry of organosilicon compounds has been studied extensively, few examples of this class of compounds with nitro substituents are known. The hydrosilylations of 3-nitropropene, 4,4,-trinitrobutene and 4,4-dinitrobutene with trichlorosilane and methyl-dichlorosilane have been reported. U.S. Pat. No. 2,756,246 describes $N_2O_3$ addition to allylsilanes, and U.S. Pat. No. 2,985,680 describes silver nitrate displacement of 3-iodopropyltriethoxysilane. The most commonly used methods of forming carbon-silicon bonds, the reaction of Grignard reagents and similar organometallics with silicon halides, and the reaction of elemental silicon with alkyl halides at high temperatures, are not compatible with nitro substituents. Polysiloxanes are usually obtained by the hydrolysis of silicon-halogen bonds, and these bonds are not stable to reaction conditions used for forming nitro silicones.

SUMMARY OF THE INVENTION

Silanes bearing gem-dinitro groups have been prepared and fluorinated. The desired silane is first prepared via a Grignard reagent containing a double bond. This permits bromination and the subsequent displacement of bromine with a nitrite ion. Oxidative nitration yields gem-dinitro compounds. Fluorination may be then accomplished with elemental fluorine or perchloryl fluoride.

Polysiloxanes are prepared by applying the nitrite displacement, oxidative nitration, and fluorination sequence to a diphenyl silane. This is prepared either (a) by brominating the hydroboration product of an unsaturated, diphenyl silane, or (b) by hydrosilation of an unsaturated silane with methyl diphenyl silane and conversion to the bromine compound through toluenesulfonate.

DESCRIPTION OF THE PREFERRED EMBODIMENT

Fluorodinitroalkyl groups attached to silicon can be prepared by nitrite displacement of a halogen precursor, oxidative nitration, and fluorination. To prepare the halogen precursor, the desired silane is prepared with a Grignard reagent and its double bond hydrobrominated.

Thus, 3-butenyltrimethylsilane, prepared from trimethylchlorosilane and the Grignard reagent of 4-bromo-1-butene, undergoes the free radical catalyzed addition of hydrogen bromide to give 4-bromobutyltrimethylsilane. The reaction of an alkyl bromide with sodium nitrite in dimethylsulfoxide gives a nitroalkane with alkyl nitrites as byproducts. This reaction proceeds smoothly with 4-bromobutyltrimethylsilane to give 4-nitrobutyltrimethylsilane. The oxidative nitration reaction of this compound gave 4,4-dinitrobutyltrimethylsilane, which, under standard aqueous fluorination conditions, gave 4-fluoro-4,4-dinitrobutyltrimethylsilane. The reaction sequence may be summarized by the following equations:

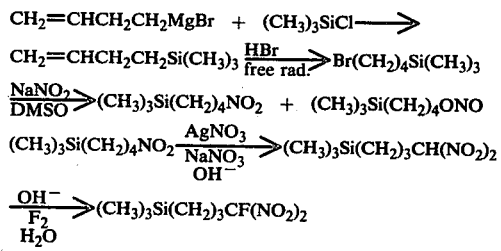

4-Bromobutyltrimethylsilane was prepared by the procedure of Perklev, Chem. Abstr., 49, 1541 (1955), involving the preparation of the Grignard reagent from 4-bromo-1-butene, its reaction with trimethylchlorosilane to give 3-butenyltrimethylsilane, and free radical catalyzed HBr addition. The latter addition gave 90% primary bromide. Using inadequate initiator gave mainly secondary bromide.

4-Nitrobutyltrimethylsilane was prepared as follows: To a solution of 1.9 g (0.028 mol) of sodium nitrite in 30 ml of dimethyl sulfoxide was added 2.92 g (0.014 mol) of 4-bromobutyltrimethylsilane. After 3 hrs, 30 ml of water was added and the mixture was extracted with three 15 ml portions of carbon tetrachloride. The carbon tetrachloride solution was washed with 10 ml of water and dried over magnesium sulfate. The NMR spectrum showed 30% nitrite ester ($CH_2ONO\delta4.57$), and 70% nitro compound. Distillation gave 1.1 g (45%) of 4-nitrobutyltrimethylsilane, bp 54°-6° (0.9 mm).

In preparing 4,4-dinitrobutyltrimethylsilane, a mixture of 0.6 g (0.015 mol) of sodium hydroxide, 2.62 g (0.015 mol) of 4-nitrobutyltrimethylsilane and 6 ml of water was stirred at 80° until a solution was formed. The solution was cooled to room temperature and 1.1 g (0.015 mol) of sodium nitrite was added. The resulting solution was added quickly to a well stirred, ice cooled mixture of 5.1 g (0.030 mol) of silver nitrate, 12 ml of water, 12 ml of ether and 2 drops of 1 N sodium hydroxide. The mixture was stirred at room temperature for 2 hrs and filtered, and the precipitate was washed with ether. The ether layer of the filtrate, combined with the washings, was dried over magnesium sulfate and distilled to give 1.9 g (57%) of 4,4-dinitrobutyltrimethylsilane, a colorless oil, bp 71°–4° (2 mm).

For 4-fluoro-4,4-dinitrobutyltrimethylsilane, fluorine diluted with nitrogen (1:5) was bubbled into an ice cooled stirred solution prepared from 1.45 g (0.0066 mol) of 4,4-dinitrobutyltrimethylsilane, 0.5 g of potassium hydroxide and 250 ml of water. When the yellow color of the solution was bleached, an additional 0.4 g of potassium hydroxide was added and the fluorination was continued until the color was bleached again. The product was extracted with three 20 ml portions of ether and dried over magnesium sulfate. Removal of the solvent gave 1.05 g (61%) of 90% pure 4-fluoro-4,4-dinitrobutyltrimethylsilane. Other analogs may be prepared using similar procedures.

The analog with one fewer methylene groups in the nitroalkyl group was prepared as follows: The reaction of chloromethyltrimethylsilane with magnesium and ethylene oxide gave 3-hydroxypropyltrimethylsilane, which, with phosphorous tribromide, gave 3-bromopropyltrimethylsilane. This compound underwent the sodium nitrite displacement smoothly, followed by the oxidative nitration and aqueous fluorination to give 3-fluoro-3,3-dinitropropyltrimethylsilane.

Compounds with more methylene groups in the nitroalkyl group may also be prepared, but the explosive is rendered less effective as the dinitro moiety is further separated from the silicon atom. The fluorination step may also be omitted, but the resultant explosives will have a decreased oxygen balance in the combustion of carbon and hydrogen in the compound. The fluorinated species of all the present compounds are therefore preferred. Use of less catalyst in the HBr addition results in a mixture of the 3- and 4-bromobutyltrimethylsilanes. The mixture was treated with sodium nitrite and the resulting mixture of nitro compounds was subjected to the oxidative nitration. The mixture of gem-dinitro compounds is separated easily because the terminal gem-dinitro compound is soluble in base; 3,3-dinitrobutyltrimethylsilane was isolated and characterized. Thus the synthesis of 3,3-dinitrobutylsilanes is shown to be feasible:

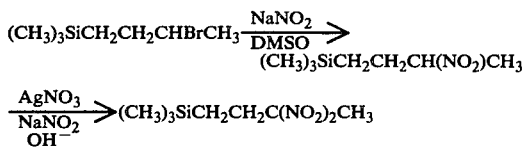

Another energetic compound within the scope of the present invention is trimethylsilylmethyl 2-fluoro-2,2-dinitroethyl ether, $(CH_3)_3SiCH_2OCH_2CF(NO_2)_2$. Attempts to prepare the compound from fluorodinitroethanol and chloromethyltrimethylsilane or iodomethyltrimethylsilane were unsuccessful. It was obtained in 45% yield from trimethylsilylmethyl trifluoromethanesulfonate (triflate) in methylene chloride in the presence of potassium carbonate.

Potassium carbonate (6 g) was added to a solution of 3.5 g (0.0148 mol) of trimethylsilylmethyl trifluoromethanesulfonate and 2.3 g of 2-fluoro-2,2-dinitroethanol in 5 ml of methylene chloride, and the mixture was stirred for 16 hrs. This suspension was added with stirring to a mixture of 30 ml of ice water and 30 ml of carbon tetrachloride. The carbon tetrachloride layer was washed with 10 ml of water, dried over magnesium sulfate, and distilled to give 1.56 g (45%) of trimethylsilylmethyl 2-fluoro-2,2-dinitroethyl ether, bp 52° (0.75 mm).

Trimethylsilylmethyl triflate was obtained from the alcohol and triflic anhydride and pyridine in methylene chloride. A solution of 4.5 g (0.0435 mol) of hydroxymethyltrimethylsilane and 3.43 g (0.0435 mol) of pyridine in 30 ml of methylene chloride was added with stirring over a 45 min. period to a solution of 12.2 g (0.043 mol) of trifluoromethanesulfonic anhydride in 30 ml of methylene chloride. After 15 min the solution was poured over ice. The methylene chloride solution was dried over sodium sulfate and distilled to give 7.0 g (68%) of trimethylsilylmethyl triflate, bp 49°–51° (9 mm). A minor byproduct of this reaction was identified as bistrimethylsilylmethyl ether, $(CH_3)_3SiCH_2OCH_2Si(CH_3)_3$. The alcohol starting material was prepared from chloromethyltrimethylsilane via its Grignard reagent. The following series of reactions illustrates the preparation of an ether of the present invention:

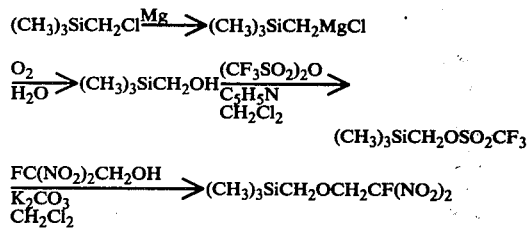

Polysiloxanes

Polysiloxanes are usually prepared by the hydrolysis of dihalosilanes, $R_2SiX_2$. The principles of the foregoing nitrite displacement of halogen, oxidative nitration and fluorination may be applied to form flurodinitropolysiloxanes, but the ease of hydrolysis of silicon-halogen bonds does not allow the use of the above procedures with silicon halogen bonds present unless a stable blocking group on silicon that can be removed after the reaction sequence and replaced by halogen is used. Carbon-silicon bonds can be cleaved by halogens and the cleavage of phenyl-silicon bonds by bromine is particularly facile.

The phenyl blocking group was applied in the preparation of methyl fluorodinitropropyl polysiloxane.

The starting material for the nitro introduction sequence, (3,bromopropyl)methyldiphenylsilane, was obtained by two different procedures. Allylmethyldiphenylsilane was prepared by the reaction of allyl magnesium bromide with chloromethyldiphenylsilane in ether. The product was hydroborated by reacting it with sodium borohydride and boron trifluoride in tetrahydrofuran, and the resulting borane was cleaved with bromine to give the bromopropyl silane, thus:

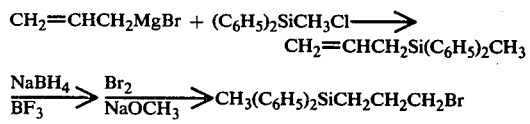

To prepare allylmethyldiphenylsilane, a solution of 1452 g (12 mol) of allyl bromide in 2.5 l of absolute ether was added dropwise with stirring, over a period of 3.5 hrs, to a suspension of 389 g (16 mol) of magnesium turnings in 2.5 l of absolute ether. An efficient reflux condenser was used, equipped with a drying tube. Excess magnesium was removed by filtration, and 1862 g (8 mol) of chloromethyldiphenylsilane was added dropwise over a 1 hr period. The solution was refluxed for 1 hr and was allowed to stand overnight at room temperature. A solution of 642 g (12 mol) of ammonium chloride in 2 l of water, and then 3 l of water were added slowly using a reflux condenser to control the exotherm. The aqueous layer was separated and extracted with three one l portions of ether. The combined ether solutions were dried over magnesium sulfate and distilled to give 1397 g (73%) of allylmethyldiphenylsilane, bp 93° (0.1 mm).

To obtain 3-(bromopropyl)methyldiphenylsilane from allylmethyldiphenylsilane, a solution (150 ml) of 29.6 g (208.3 mol) of boron trifluoride etherate in dry tetrahydrofuran was added over a 1 hr period, with stirring, to 350 ml of a tetrahydrofuran solution of 119 g (0.50 mol) of allylmethyldiphenylsilane and 5.94 g (0.156 mol) of sodium borohydride. The reaction mixture was heated at reflux for 2.5 hrs and then 10 ml of methanol was added. Then, 27.3 ml (0.50 mol) of bromine and sodium methoxide solution (from 14.4 g, 0.625 mol of sodium and 300 mol of methanol) were added simultaneously at such a rate as to maintain a yellow color in the reaction mixture. The reaction temperature was kept at 25°–30° by means of an ice bath. The reaction mixture was poured into a mixture of 250 ml of 50% potassium carbonate and 250 ml of cyclohexane. The mixture was agitated until the strong yellow color faded. The layers were separated and the aqueous layer was extracted with three 100 ml portions of cyclohexane. The combined organic layers were washed with three 300 ml portions of water and with 150 ml of saturated sodium chloride, dried over potassium carbonate, and distilled to give 79 g (49.5%) of (3-bromopropyl) methyldiphenylsilane, mp.176°–210° (0.3 mm).

Another procedure, which appears to be more readily adaptable to scale-up, involves the addition of methyldiphenylsilane to allyl acetate, catalyzed by chloroplatinic acid, to give (3-acetoxypropyl) methyldiphenylsilane. The ester was hydrolyzed with base to give (3-hydroxypropyl)methyldiphenylsilane. This may be carried out without isolating the ester. p-Toluenesulfonyl chloride and pyridine in methylene chloride converted this alcohol to the p-toluenesulfonate, which, with lithium bromide in dimethyl sulfoxide, gave the desired bromide. The reaction sequence may be illustrated as follows:

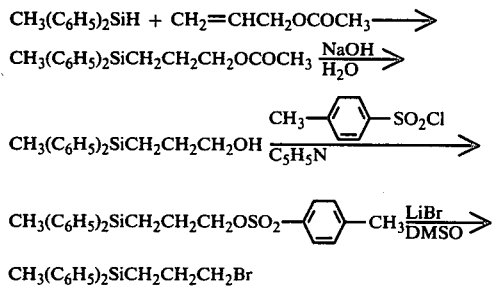

Methyldiphenylsilane (100 g, 0.49 mol) was added at 90° over a period of 4 hrs, with stirring, to a mixture of 100 g (1.0 mol) of allyl acetate and 0.10 ml of a 0.1 M chloroplatinic acid solution in isopropanol. When half of the methyldiphenylsilane was added an additional 0.10 ml of the chloroplatinic acid solution was added. Excess allyl acetate was distilled 15 min. after the addition was completed. The residue was dissolved in 150 ml of methanol and a solution of 20 g of sodium hydroxide in 40 ml of water was added dropwise. After the mixture was stirred for 2 hrs, 200 ml of water was added, and the mixture was neutralized with hydrochloric acid. The product was extracted with methylene chloride, dried over magnesium sulfate and distilled to give 65 g (50%) of (3-hydroxypropyl) methyldiphenylsilane, bp 130°–140° (0.03 to 0.07 mm). p-Toluenesulfonyl chloride 3.5 g, 0.184 mol) was added to a solution of 29 g (0.118 mol) of (3-hydroxypropyl)methyldiphenylsilane and 14.6 g (0.184 mol) of pyridine in 60 ml of methylene chloride at 0°. The mixture was kept at 0°–5° for 18 hrs and 40 ml of ice water was added. The water layer was extracted with 40 ml of methylene chloride, and the combined organic layers were washed with 2–30 ml portions of water. Solvent was removed and the product was crystallized from ether to give 46 g (95%) (3-propyl)methyldiphenyl p-toluenesulfonate, mp 68°–69°.

To obtain (3-bromopropyl)-methyldiphenylsilane from the toluenesulfonate, a solution of 3.5 g (0.04 mol) of lithium bromide and 5.98 g (0.0146 mol) of (3-propyl) methyldiphenylsilane p-toluenesulfonate in 25 ml of dimethyl sulfoxide was stirred at ambient temperature for 3 hrs. Water (10 ml) was added and the product was extracted with three 10 ml poritons of carbon tetrachloride. The combined organic layers were washed with 10 ml of water, dried and stripped of solvent. The residue consisted of 4.2 g (90%) of 90% pure (3-bromopropyl)-methyldiphenylsilane.

Allyloxytrimethylsilane ($CH_2$=$CHCH_2OSi(CH_3)_3$) may be substitute for allyl acetate and tris (triphenylphosphine) rhodium chloride may be substituted for chloroplatinic acid as the catalyst. Improved yields are obtained with both these compounds. Sodium bromide, rather than the more expensive lithium bromide may be used for the bromination. The analogous silane system with two fluorodinitropropyl groups may be prepared. The most practical route is shown in the following reaction sequence:

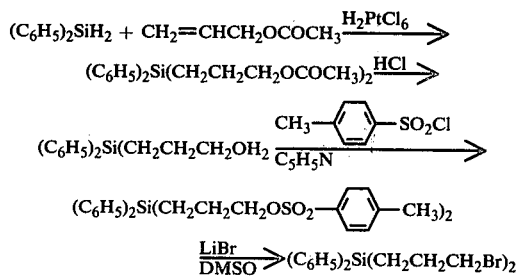

The starting material diphenylsilane was prepared by the reduction of commercial dichlorodiphenylsilane with lithium aluminum hydride in ether solvents. A more preferred method involves the use of [($C_6H_5$)$_3$P]$_3$ RhCl as the catalyst and $CH_2$=$CHCH_2OSi(CH_3)_3$. Yields by NMR were in the 70–85% range. Either lithium or sodium bromide may be used, and water improves bromination.

To begin the nitro induction sequence, the bromosilane or dibromosilane is reacted with sodium nitrite in dimethyl sulfoxide. With (3-bromopropyl)methyldiphenylsilanes a maximum yield is observed after a 40 min reaction period, with a slow loss of product in prolonged reactions. The corresponding nitrite and alcohol is also formed and the nitrite is slowly hydrolyzed to the alcohol under the reaction conditions. The DMSO may be from the previous solution (3-Nitropropyl)methyldiphenylsilane is obtained:

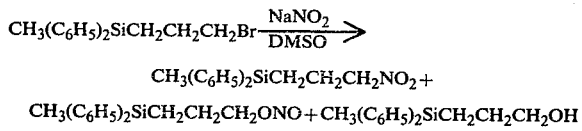

Addition of 99.6 g (1.26 mol) of sodium nitrite to a solution of 101 g (0.317 mol) of (3-bromopropyl) methyldiphenylsilane in 500 ml of dimethyl sulfoxide resulted in a temperature rise to 30° over a 40 min period. The mixture was added to 2.5 l of water and the product was extracted with four 300 ml portions of carbon tetrachloride. The carbon tetrachloride solution was washed with three 600 ml portions of water and with 300 ml of saturated sodium chloride, and the solvent was removed. The NMR spectrum of the residue showed a 52% yield of the nitro compound (δ4.2) a 20% yield of the nitrite (δ4.4) and a 15% yield of the alcohol and/or bromide (δ3.3).

The mixture was stirred for 1 hr with 80 ml of 5 N potassium hydroxide and 320 ml of water was added. The mixture was extracted with two 100 ml portions of ether. The aqueous solution was acidified to pH 6 with acetic acid and the product was extracted with four 100 ml portions of methylene chloride. The methylene chloride solution was dried over magnesium sulfate and evaporated to give 45.4 g (50%) of (3-nitropropyl) methyldiphenylsilane. An analytical sample was obtained by molecular distillation: bp 152° (0.22 mm).

The oxidative nitration of (3-nitropropyl) methyldiphenylsilane posed no special problems if relatively concentrated potassium hydroxide was used initially to form the salt of the starting material. A 70% yield of (3,3-dinitropropyl)methyldiphenylsilane was obtained as well as 8% recovered starting material. The reaction is represented as follows:

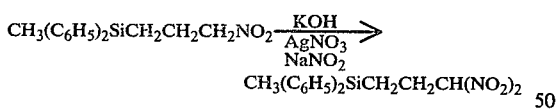

The aqueous fluorination of salts of this dinitro compound did not prove to be satisfactory because of acid-forming side reactions. The potassium salt was fluorinated readily, however, when perchloryl fluoride was used as the fluorinating agent using the reaction conditions developed by Kamlet and Adolph, *J. Org. Chem.*, 33, 3073 (1968). The perchloryl fluoride was absorbed completely until the reaction was complete, and a 79% yield of (3-fluoro-3,3-dinitropropyl) methyldiphenylsilane was isolated from the following reaction:

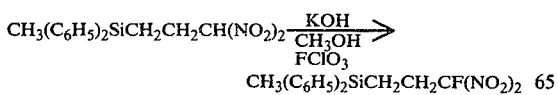

(3,3-Dinitropropyl)methyldiphenylsilane was dissolved in a solution of 0.217 mol of potassium hydroxide in 900 ml of methanol. The solution was placed in a 2 l flask equipped with a glass dip tube for introducing perchloryl fluoride, a thermometer, a magnetic stirrer and an ice bath. The flask was vented to the fume-hood atmosphere by means of a mineral oil bubbler, and another bubbler as well as an inverted vacuum trap (to prevent suck back) were placed between the dip tube and a perchloryl fluoride cylinder. Perchloryl fluoride was passed into the solution at 10° until it was no longer absorbed (2 hrs). Then, 1000 ml of water was added and the solution was allowed to stir 1 hr at room temperature. An additional 1500 ml of water was added and the mixture was made basic (pH 12) with potassium hydroxide. The product was extracted with four 400 ml portions of methylene chloride. The methylene chloride solution was washed with three 1000 ml portions of water, dried and stripped of solvent. The residue, 58.5 g, was chromatographed on a 750 g column of dry silica gel, using carbon tetrachloride (30 l) for elution, to give 44.5 g (79%) of (3-fluoro-3,3-dinitropropyl)methyldiphenylsilane.

Dephenylation of (3-fluoro-3,3-dinitropropyl) methyldiphenylsilane was accomplished by heating it at 100° with excess bromine. This reaction, as shown below, gave a 78% yield of (3-fluoro-3,3-dinitropropyl) methyldibromosilane, which was characterized by proton and fluorine NMR, although it was too hygroscopic for elemental analysis:

CH$_3$(C$_6$H$_5$)$_2$SiCH$_2$CH$_2$CF(NO$_2$)$_2$
$^{Br_2}$CH$_3$Br$_2$SiCH$_2$CH$_2$CF(NO$_2$)$_2$

When two dinitrofluoroalkyl groups are present, addition of water to the bromination mixture improves dephenylation. Methylene chloride and acetic acid were used as solvents.

Hydrolysis of this dibromosilane with ice gave an oil that was shown by cryoscopic molecular weight determination (834) and by elemental analysis to consist of a mixture of cyclic polysiloxanes, with from three to five, with an average of four silicon atoms, as shown:

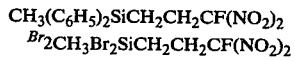

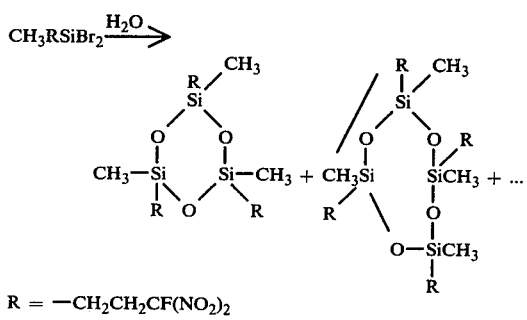

R = —CH$_2$CH$_2$CF(NO$_2$)$_2$ (3-Fluoro-3,3-dinitropropyl)methyldifluorosilane was obtained in 80% yield from the preceding polysiloxanes resulting from the hydrolysis of the dibromide by the use of HF or NaF in ethanol:

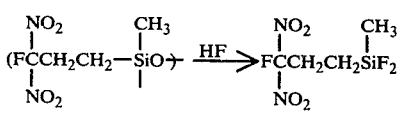

This monomer may also be obtained directly from the dibromide in its crude form resulting from dephenylation.

The inertness of silicon fluorides toward acids was utilized to prepare the dimeric fluoride. Thus, the difluoride reacted with sodium methoxide in methanol to give the methoxy fluoride. This methoxy group was cleaved by aqueous acid, whereas the fluoride was stable, yielding the dimer:

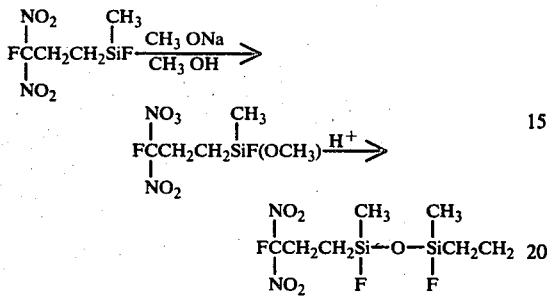

Other polymerization conditions may be used. The use of hyrated sodium sulfate on cuprous chloride gave products with an average of five units per molecule.

The use of 75% sulfuric acid as the reaction medium, reported to give high polymers with dimethylsilicones, yielded a 5.7 unit polymer. A similar product was obtained with 30% fuming sulfuric acid and with concentrated HCl in refluxing ethanol. Dibromosilane was reacted with one equivalent of methanol to form the methoxybromosilane. After addition of the ferric chloride catalysts, polymers of 4.8 to 5.6 units were obtained. Copolymerization of dibromosilane and phenyl-dimethylethoxysilane under the same conditions produced a substance with a molecular weight of 1713.

The hydrolysis of the dibromide was also carried out under basic conditions and oligomers of 4–6 units were obtained. Ammonium hydroxide, sodium bicarbonate, potassium carbonate and potassium hydroxide were used as reagents and other, dioxane, water, toluene and carbon tetrachloride as solvents.

Fluorosilanes differ in reactivity from other halosilanes in that they are not hydrolyzed readily under neutral or acidic conditions, but are reactive toward base. This selectivity offers possibilites for the preparation of polymers. The hydrolysis of $CH_3SiF_2CH_2CH_2CF(NO_2)_2$ with sodium hydroxide in the presence of methylene chloride gave a 4.3 unit product, but in 20% aqueous ethanol, a 6.1 unit product was obtained. Higher polymers from (3-fluoro-3,3-dinitropropyl) methyl siloxane oligomers were best obtained when the intital dibromide hydrolysis was carried out in the absence of organic solvents or in the presence of methylene chloride, shown previously to give mainly trimer. Heating this material with powdered sodium hyroxide at 150° was found to give a molecular weight maximum in 24 hrs of 10.6 monomer units. Potassium hydroxide, sodium trimethylsilanate, and tetramethylammonium trimethylsilanate also catalyzed the reaction but not as effectively as sodium hydroxide. Sodium hydride was found to be as effective as sodium hydroxide and is preferred because of the ease with which small quantities can be manipulated. Hydrocarbon solvent for the bromide hydrolysis gave results similar to methylene chloride, but sulfuric acid, aqueous ethanol, acetone and carbon tetrachloride were not as satisfactory. Organic bases did not function successfully as catalysts with oligomers that were polymerized with NaOH or NaH.

Higher molecular weight polymer fractions were found to be insoluble in ether, and extraction of materials with molecular weights of 1600 to 2000 in this way gave products with molecular weights to over 3,000 heating polymer samples with additional catalyst resulted in a decrease in molecular weight. The copolymerization of $FC(NO_2)_2CH_2CH_2SiBrCH_3$ with $C_6H_5SiCl_3$ in equimolar amounts gave a product with a molecular weight of 4074.

A method by which commercial silicones are crosslinked is hydrogen abstraction by free radical initiators. This method was explored with the nitro-containing materials using benzoyl peroxide, and in one case a doubling of molecular weight was observed. This method may be useful with high molecular weight linear polysiloxanes.

What is claimed is:

1. A compound of the formula $$(R_1)_3 \, Si \, R_2 \, CF \, (NO_2)_2$$

wherein the $R_1$ groups may be the same or different and are $C_6H_5$ or $CH_3$; and $R_2$ is $(CH_2)_2, (CH_2)_3$, or $CH_2OCH_2$ 2. An explosive composition comprising a compound of claim 1.

3. A polymer prepared by hydrolyzing

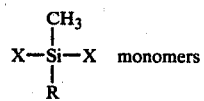 monomers wherein R is $CH_2CH_2CF(NO_2)_2$ and X is halogen.

4. A process for the preparation of fluorodinitroalkyl silicon compounds comprising the steps of:
 (a) preparing $(R_1) \, SiR_2CH_2Br$;
 (b) nitrating $(R_1)_3SiR_2CH_2Br$ with $NO_2$ in DMSO to form $(R_1)_3SiR_2CH_2NO_2$;
 (c) nitrating $(R^1)_3SiR_2CH_2NO_2$ with $AgNO_3$ and $N_aNO_2$ to form $(R_1)_3SiR_2CH(NO_2)_2$; and
 (d) fluorinating $(R_1)_3SiR_2CH(NO_2)_2$ to form $(R_1)_3SiR_2CF(NO_2)_2$;
 wherein the $R_1$ groups may be the same or different and are $C_2H_5$ or $CH_3$; and
 $R_2$ is $(CH_2)_2$ or $(CH_2)_3$.

5. The process of claim 4 wherein $(R_1)_3SiR_2CH_2Br$ is prepared from $(R_1)_3SiR_2=CH_2$.

6. The process of claim 4 wherein said fluorination is under aqueous conditions.

7. The process of claim 4 wherein said fluorination employs perchloryl fluoride.

8. The process of claim 4 wherein at least 2 $R_1$ groups are $C_6H_5$ and further comprising the steps of:
 dephenylation to replace at least 2 $R_1$ phenyl groups with Br; and
 hydrolysis of the preceding bromine compound to form a cyclic polysiloxane.

9. A process for preparing gem-dinitro polysiloxanes comprising the steps of:
 (a) preparing a hydroxy diphenyl silane from a diphenyl silane;
 (b) converting a hydroxy diphenyl silane to the corresponding p-toluenesulfonate;

(c) replacing said p-toluenesulfonate with bromine to form a bromosilane;

(d) displacing said bromine from the bromosilane with nitrite to form a nitro compound;

(e) oxidatively nitrating said nitro compound to form a gem-dinitro silane; and (f) dephenylating and hydrolyzing said gem-dinitro silane.

10. The process of claim 9 further comprising the step of fluorinating said gem-dinitro silane.

11. The process of claim 9 wherein said preparing a hydroxy diphenyl silane is catalyzed with tris (triphenylphosphine) rhodium chloride.

12. The cyclic compound having the formula:

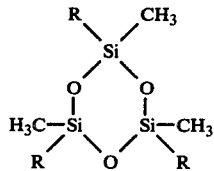

wherein R is $CH_2CH_2CF(NO_2)_2$.

13. The cyclic compound having the formula:

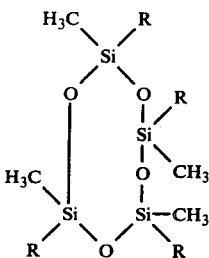

wherein R is $CH_2CH_2CF(NO_2)_2$.

14. The cyclic compound having the formula:

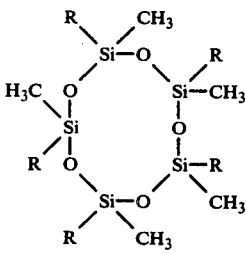

wherein R is $CH_2CH_2CF(NO_2)_2$.

15. An explosive composition comprising the compound of claim 12.

16. An explosive composition comprising the compound of claim 13.

17. An explosive composition comprising the compound of claim 14.

* * * * *